United States Patent
Spielberg

(10) Patent No.: US 7,018,419 B2
(45) Date of Patent: Mar. 28, 2006

(54) MICROPOROUS ENCAPSULATED ENDOCRINE CELL DISKS, BICONCAVE DISKS AND MULTIDIMPLED CHAMBERS FOR HORMONAL REPLACEMENT

(76) Inventor: Theodore E. Spielberg, 10 Pinewood Cir., Wellesley, MA (US) 02181

( * ) Notice: Subject to any disclaimer, the term of this patent is extended or adjusted under 35 U.S.C. 154(b) by 493 days.

(21) Appl. No.: 09/928,392

(22) Filed: Aug. 13, 2001

(65) Prior Publication Data

US 2001/0049130 A1    Dec. 6, 2001

Related U.S. Application Data

(63) Continuation of application No. 09/397,780, filed on Sep. 16, 1999, now abandoned, which is a continuation of application No. 08/589,860, filed on Jan. 22, 1996, now abandoned, which is a continuation of application No. 08/246,676, filed on May 20, 1994, now abandoned.

(51) Int. Cl.
*A61F 2/02* (2006.01)
*C12N 5/00* (2006.01)
*A61K 35/39* (2006.01)

(52) U.S. Cl. .................. 623/23.72; 435/325; 424/556; 514/866

(58) Field of Classification Search ............. 623/23.64, 623/23.73, 23.72; 424/562, 556, 422, 423, 424/424, 425, 489; 435/174, 177, 182; 514/866
See application file for complete search history.

(56) References Cited

U.S. PATENT DOCUMENTS 5,855,613 A * 1/1999 Antanavich et al. ..... 623/23.72
5,879,709 A * 3/1999 Soon-Shiong et al. ...... 424/484
6,165,225 A * 12/2000 Antanavich et al. ..... 623/23.72

OTHER PUBLICATIONS

Yang et al. (Biomaterials, Jan. 1994, vol. 15(2): 113-120.).*

* cited by examiner

*Primary Examiner*—Gary B. Nickol
(74) *Attorney, Agent, or Firm*—Cesari and McKenna, LLP

(57) ABSTRACT

An endocrine cell microdisk or macrodisk containing pancreatic cells for transplantation into an animal body is formed with a lateral extent much greater than its thickness to thereby enhance its diffusional capability. One or more concavities may also be formed therein to further enhance the diffusion of cellular products across the microdisk walls.

6 Claims, 2 Drawing Sheets

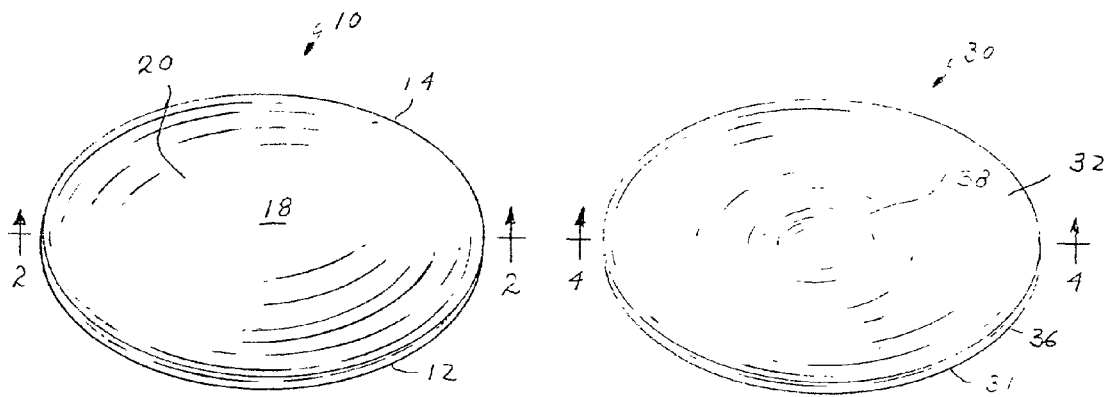
FIG. 1
FIG. 3
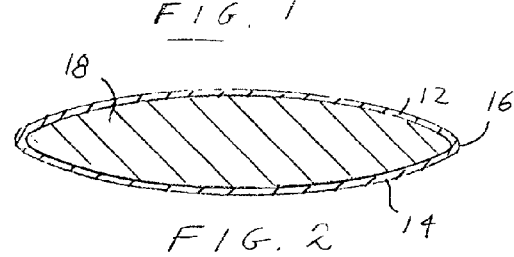
FIG. 2
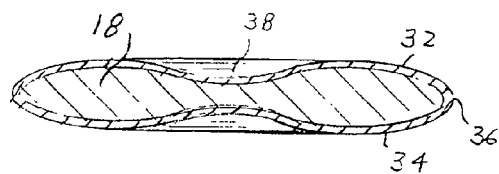
FIG. 4
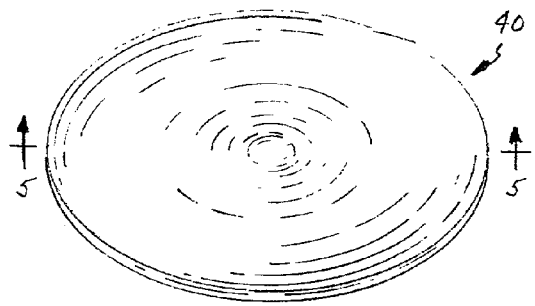
FIG. 5
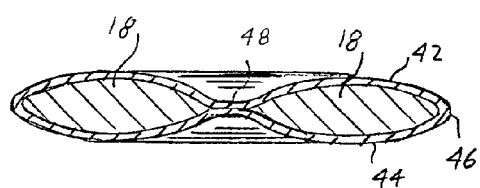
FIG. 6
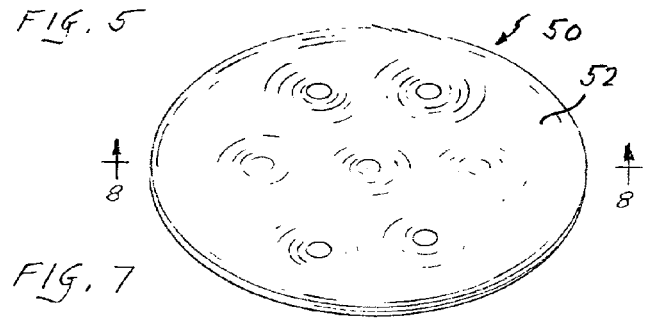
FIG. 7
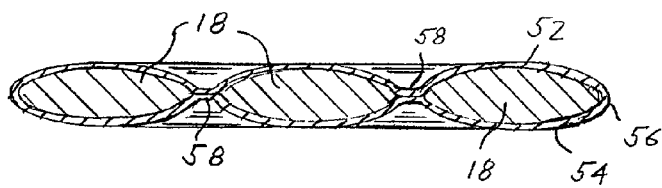
FIG. 8

MICROPOROUS ENCAPSULATED ENDOCRINE CELL DISKS, BICONCAVE DISKS AND MULTIDIMPLED CHAMBERS FOR HORMONAL REPLACEMENT

This application is a continuation of U.S. patent application Ser. No. 09/397,780, filed Sep. 16, 1999 (abandoned), which is a continuation of U.S. patent application Ser. No. 08/589,860 filed Jan. 22, 1996 (abandoned), which is a continuation of U.S. patent application Ser. No. 08/246,676, filed May 20, 1994 (abandoned).

BACKGROUND OF THE INVENTION

A. Field of the Invention

The invention relates to cell transplantation in an animal body, and comprises a carrier for cells to be implanted.

B. Prior Art

Attempts have been made to create mechanical immune barriers for transplantation of endocrine cells. In these devices, microporous membranes separate the transplanted cells from the host's immune rejecting cells and proteins (immunoglobulins) but allow desired nutrients and oxygen to sustain these cells and the desired hormonal products produced by the cells to benefit the host. The main application of these hybrid devices is in the treatment of diabetes mellitus in which an insulin deficiency in the host is treated by transplanting insulin producing beta cells from the islets of Langerhans of the pancreas contained within the devices.

In general, there have been three principal types of microporous hybrid endocrine devices, namely, devices that are incorporated in a vascular shunt; macroencapsulated devices in which clusters of endocrine (islet) cells are enclosed in a microporous membrane; and microencapsulated devices in which a single or small number of endocrine cells (islets) are enclosed in a spherical microporous membrane. In all three types of devices, allographs or xenographs have been used.

These devices have shown promising results in reducing or eliminating the need for exogenous insulin therapy in diabetic animals; however, because of poor diffusional characteristics, none of these devices have been shown to respond rapidly enough to post prandial or fluctuating blood glucose levels to affect the tight glucose control necessary to prevent the long term complications of diabetes, such as nephropathy, neuropathy, premature atherosclerosis, and retinopathy and blindness.

In this invention, a novel micro and macro encapsulation geometry is described which overcomes these deficiencies.

DETAILED DESCRIPTION OF THE INVENTION

A. Objects of the Invention

Accordingly, it is an object of the invention to provide an encapsulated pancreatic beta cell or cells with markedly enhanced diffusional properties.

Further, it is an object of the invention to provide an encapsulated endocrine cell or cells with enhanced hormonal response to stimuli as in blood sugar levels for pancreatic beta cell production of insulin.

Still a further object of the invention is to provide an encapsulated endocrine or pancreatic beta cell or cells with enhanced ability to receive sustaining oxygen and nutrients to promote prolonged survival and avoid cellular dysfunction or death within the device.

Still a further object of the invention is to provide an encapsulated endocrine or pancreatic beta cell or cells capable of being stacked to reduce the volume requirement of such transplants.

B. Brief Summary of the Invention

In accordance with the present invention, an encapsulated endocrine or pancreatic cell or cells is formed from a microporous encapsulation in the form of a disk of substantial extent in relation to its thickness and enclosing one or more insulin producing islet cells.

Preferably, the disk has a ratio of diameter to thickness of at least four and more preferably on the order of from six to twenty. The disk-shaped nature of the encapsulation, in contrast to prior spherical encapsulations, significantly increases the surface to volume ratio of the encapsulation, and thus increases the diffusional capacity of the enclosed cellular material.

Moreover, when transplanted in a, body cavity with large surfaces (vascular membranes) such as the peritoneal cavity, the disks align themselves along the surfaces on one of their flat sides, increasing the surface is area of the device in contact with the vascular surface and reducing the diffusion distance. This further enhances the diffusion rate of oxygen and carbon dioxide, as well as nutrients, and glucose and insulin between the host and the microdisk resulting in increased efficiency as well as increased support of the enclosed transplanted endocrine cell.

Thus, the endocrine cell disk achieves increased efficiency and support intrinsically on the basis of its favorable geometry with increased surface to volume ratio as well as its enhanced interaction with vascular body surfaces as a result of its increased contact area. Additionally, when transplanted in smaller body cavities, such as the renal capsule, the endocrine cell disks can be stacked, allowing more endocrine cells per unit area than could be achieved with other structures, e.g., microspheres. This allows the transplantation of more endocrine cells at a given body site delivering more hormone, and may obviate the need for utilization of multiple sites and multiple surgical procedures.

In a preferred embodiment, the endocrine cell disk is further characterized by one or more concave faces on opposite surfaces thereof to further enhance the ratio of the transverse extent of the major surfaces to its thickness to thereby increase the ratio of surface area to volume. This may be accomplished by forming the disk of a material which maintains its structural integrity after formation into the desired shape, or it may be accomplished by fusing or otherwise joining opposed faces of the disk at one or more portions thereof. This increases the surface to volume ratio of the device while preserving its stacking ability.

For example, comparing a cell microsphere with a cell biconcave microdisk of the same total volume of 90 microns cubed, as in the erythrocyte, the surface area of the microsphere is 98 microns squared, while the surface area of the biconcave microdisk (erythrocyte) is 140 microns squared.

In the larger macroencapsulated version, disks, as well as other shapes, may be employed as long as they have two opposing flattened sides with one or more surface concavities creating a dimpled or multidimpled chamber for endocrine cell encapsulation.

The devices of the present invention may be either directly transplanted into the body of a patient such as in the peritoneal cavity or may be enclosed in a supporting structure (membrane) to aid in insertion and removal or to improve vascularization, or to support their favorable geometry.

DETAILED DESCRIPTION OF THE INVENTION

The foregoing and other objects and features of the invention will be more readily understood on reference to the following detailed description of the invention, when taken in connection with the accompanying drawings, in which FIG. 1 is a view in perspective of a preferred form of cell-encapsulating disk in accordance with the present invention;

FIG. 2 is a vertical cross-sectional view through the disk of FIG. 1;

FIG. 3 is a view in perspective of a second embodiment of cell-encapsulating disk in accordance with the present invention;

FIG. 5 is a view in perspective of still another embodiment of disk in accordance with the present invention;

FIG. 6 is a vertical cross-sectional view through the disk of FIG. 5;

FIG. 7 is a view in perspective of still another embodiment of disk in accordance with the present invention;

FIG. 8 is a vertical cross-sectional view through the disk of FIG. 7.

Figure 4A:
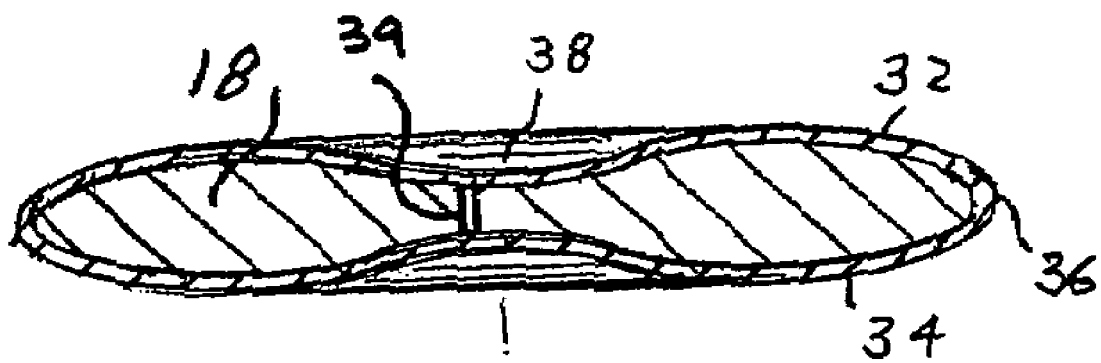
FIG. 4 is a vertical cross-sectional view through the disk of FIG. 3.

For descriptive purposes, macrodisks, as well as microdisks will be described, although the macrodisks may assume other flattened shapes. Since the main application of this device is as an artificial endocrine pancreas for the treatment of diabetes mellitus, an insulin secreting device is described, though the invention is applicable to any endocrine cell producing a hormone.

Turning now to FIG. 1, a cell-encapsulating disk in accordance with the present invention comprises a generally circular shell or casing 10 of limited thickness and significantly greater extent (i.e., linear dimension measured transverse to the thickness) formed from an upper face or surface 12 and a lower face or surface 14. These faces are joined together along their periphery 16 to form a continuous chamber 18 within the interior thereof for enclosing and encapsulating cellular material 20.

The cellular material 20 may comprise, for example, insulin producing islet cells (beta cells) which have been separated from the exocrene pancreas by collagenase digestion and purified by density gradient centrifugation as is well-known in the art. The material forming the disk 10 may be formed from a variety of materials that are microporous and thus allow the discharge of cell products such as insulin, as well as waste products, across the cell wall, as well as the passage of nutrients to the cell through the cell wall. Some substances well-known in the microencapsulating art that may be used in the present invention are alginate, barium alginate, alginate polyaminoacid, alginate-polylysine-alginate, agarose, agarose-polystyrene, hydrogels, polyion complexes, and polymers such as hydroxyethylmethacrylate-methylmethacrytate (HEMA-MMA), and AN 69 (polyacrylonitrile); other substances may also be used as appropriate.

Unlike prior encapsulating techniques which use a generally spherical encapsulating shell, the encapsulating shell of the of the present invention is discoid shaped, that is, it has substantially different dimensions in each of two perpendicular directions. In particular, the transverse extent of the shell (i.e., its diameter) is substantially larger than its thickness, preferably by a least a factor of four, and desirably from six to twenty. This significantly increases the diffusional rate between the enclosed cell or cells and its environment. As is known to those skilled in the art, the diffusion rate across a membrane is proportional to $c*A*T/d*M$, where c is the concentration difference between the exterior and interior surfaces of the membrane, A is the area of the membrane across which diffusion occurs, T is the temperature, d is the distance across which diffusion occurs, and M is the molecular weight of the diffusing material; the symbols "*" and "/" denote multiplication and division, respectively. The disk of the present invention significantly increases the surface area A in relation to the volume of the disk, and thus greatly increases its diffusional capability as contrasted to the hitherto-utilized spherical cells. The structure of FIG. 1 is intended for disks containing one or more cells, up to a disk size of approximately 2000 microns in diameter (microdisk).

The diffusional capacity of the disk of the present invention is further enhanced by forming it with one or more surface concavities. In particular, as shown in FIGS. 3 and 4, a disk 30 has upper and lower surfaces 32, 34 joined together at the periphery 36 to form a cell-encapsulating structure in a manner similar to that of FIG. 1. One or both of the opposing faces 32, 34 are invaginated, i.e., turned inwardly toward each other, to form concave portions 38 on one or both sides of the disk, respectively. As was the case with FIG. 1, the transverse extent of the shell (i.e., its diameter) is substantially larger than its thickness, preferably by a least a factor of four, and desirably from six to twenty. The shape of the disk of FIGS. 3 and 4, which resembles that of an erythrocyte, provides an even larger surface-to-volume ratio than that of the disk of FIGS. 1 and 2, and thus provides an enhanced diffusional capability. The disk of FIGS. 3 and 4 is intended for use both as microdisks (i.e., disks of less than about 2000 microns in diameter), as well as for larger macrodisks (i.e., disks of greater than about 2000 microns in diameter).

The concave shape of the microdisk of the present invention may be provided in a variety of ways. For example, if the interior cavity 18 of the disk of FIGS. 1 and 2 is not completely filled with cellular and related material, one or more of the opposed faces 12 and 14, when formed of sufficiently thin and pliable material, will conform itself generally to the surface of its liquid contents, thus assuming at least a "saucer" shape. On the other hand, if the faces of the disk are of sufficient thickness and strength, the disk may be molded with the concavity formed in place. Alternatively, an interior structural element 39 (FIG. 4A), e.g., a thin, flat tab or a thin column may be extended across the disk from one face thereof to the other in the interior of the disk to thereby restrict the spacing of the faces at the location of the column when the disk is filed with liquid cellular material. Those portions of the disk faces in the vicinity of the column will thereby assume a concave geometry relative to more remote portions of the opposed faces which will assume a generally convex geometry as the disk is filled. These columns may be provided at a number of locations within the disk so to form a number of concavities.

FIGS. 5 and 6 show yet another embodiment of the present invention in which the invaginated shape of the disk faces is maintained by fusing or otherwise joining the faces together at one or more points. In particular, the disk 40 has upper and lower faces 42, 44, respectively, joined at their periphery 46 to form an enclosed chamber containing one or more cells. The opposing faces 42, 44 of the disk are fused or otherwise joined together at the center 48 in order to maintain the concavity of the disk faces and thereby maintain a larger area/volume ratio of the disk.

It should be noted that the manner of joinder shown in FIGS. 5 and 6 maintains the disk as a single chamber structure which allows the contents to communicate with each other, while preserving the shape of the disk. The size of the disk may vary from just sufficient to accommodate as few as one or two cells (e.g., micron sized) to sufficient to accommodate tens of thousands of cells (e.g., an inch or more in diameter).

As the size of the disk increases, the number of joining points is required to maintain a surface with significant concavities increases. FIG. 7 shows a disk 50 formed from an upper face 52 joined to a lower face 54 around the periphery 56 thereof. Concave depressions 58 are formed by fusing or otherwise joining the surfaces 52, 54 to each at spaced apart locations throughout the extent of the capsule. The resultant structure is characterized by a high surface to volume ratio while maintaining a single continuous cavity.

Although I have described the preferred form of my invention as comprising a discoid of generally circular shape, particularly for smaller (micron-sized) microencapsulations, other shapes, e.g., square or rectangular "pads" may also be used, particularly in larger "macrodisks", as long as the lateral extent of the structure (i.e., its diameter or width) is much greater than its thickness.

It is understood that an (insulin producing) endocrine cell may be a naturally occurring cell or an artificial endocrine (beta) cell created by transfection of a (insulin) gene. It will also be understood that the microporous membrane need not transport material through actual visible pores but may in fact transfer material through solubilization mechanisms.

From the foregoing, it will be seen that microporous encapsulated endocrine cell microdisks and uniconcave or biconcave microdisks have significantly superior diffusional, tissue contact, and stackability characteristics, that allow for more rapid hormonal response (insulin) to physiologic stimuli (glucose) and allow for the transplantation of more microencapsulated endocrine cells per unit of body space. Yet they can be readily manufactured with modifications in the well-known art of spherical microencapsulation. Larger multidimpled "discoid" chambers or "macrodisks" with superior diffusional characteristics resulting from their favorable geometry are also described.

What is claimed is:

1. An endocrine cell microdisk comprising a microporous membrane having first and second opposed faces joined together at the periphery thereof and forming an extended structure of lateral extent substantially greater than the maximum thickness between the surfaces and containing endocrine cellular material for implantation as a unit into an animal body, at least one of said faces being formed to project concavely toward the other.

2. An endocrine cell microdisk according to claim 1 in which said lateral extent is at least four times said thickness.

3. An endocrine cell microdisk according to claim 1 in which said microdisk is formed generally in the shape of an erythrocyte.

4. An endocrine cell microdisk according to claim 1 which includes at least one internal joining structure extending between said opposed faces and maintaining a concavity in at least on of said faces.

5. An endocrine cell microdisk according to claim 4 includes a plurality of internal joining structures extending between said opposed faces and maintaining a plurality of concavities in at least one of said faces.

6. An endocrine cell microdisk according to claim 1 in which opposed faces of said disk are joined to each other at a plurality of locations on said faces to thereby form a multiplicity of concavely-extending surface portions.

* * * * *